US006645229B2

(12) United States Patent
Matsumura et al.

(10) Patent No.: US 6,645,229 B2
(45) Date of Patent: Nov. 11, 2003

(54) SLIMMING DEVICE

(75) Inventors: Yuko Matsumura, Takatsuki (JP); Yasuhiro Sato, Kobe (JP); Hideo Iwata, Kyotanabe (JP); Toshihide Yoshida, 125-4 Nishigamo-Sumiyashiro-cho, Kita-ku, Kyoto (JP)

(73) Assignees: Matsushita Electric Works, Ltd., Osaka (JP); Toshihide Yoshida, Kyoto (JP)

( * ) Notice: Subject to any disclaimer, the term of this patent is extended or adjusted under 35 U.S.C. 154(b) by 84 days.

(21) Appl. No.: 09/739,818

(22) Filed: Dec. 20, 2000

(65) Prior Publication Data

US 2001/0014815 A1 Aug. 16, 2001

(30) Foreign Application Priority Data

Dec. 22, 1999 (JP) .......................................... 11-364324

(51) Int. Cl.[7] ............................ A61F 7/00; A61H 23/02

(52) U.S. Cl. ............................... 607/1; 607/96; 607/88; 607/90; 607/100

(58) Field of Search ............................ 607/1, 3, 96, 19, 607/77, 100, 108, 90, 88, 97, 98

(56) References Cited

U.S. PATENT DOCUMENTS 4,742,235 A * 5/1988 Koji ............................ 607/90
4,966,450 A * 10/1990 Mori ........................... 607/88
5,018,521 A * 5/1991 Campbell .................... 607/98
5,616,140 A * 4/1997 Prescott ....................... 607/91
6,024,760 A * 2/2000 Marchesi ..................... 607/96

FOREIGN PATENT DOCUMENTS

| | | | |
|---|---|---|---|
| DE | 968501 | 2/1958 | |
| DE | 3616274 | 11/1987 | |
| DE | 3715269 | 12/1987 | |
| EP | 695559 | 2/1996 | |
| EP | 1 110 532 A2 * | 6/2001 | .......... A61H/23/02 |
| JP | 9-248213 | 9/1997 | |
| JP | 9-276354 | 10/1997 | |
| WO | 85/03634 | 8/1985 | |

OTHER PUBLICATIONS

Patents Abstracts of Japan, vol. 1998, No. 2, Jan. 30, 1998 (English Abstract of JP 9–276354).
Patent Abstracts of Japan, vol. 1998, No. 1, Jan. 30, 1998 (English Abstract of JP 9–248213).
Database WPI, Week 199748, AN 1997–520761, Derwent Publications Ltd., London, GB (English Abstract of JP 9–248213).

* cited by examiner

*Primary Examiner*—Hieu T. Vo
(74) *Attorney, Agent, or Firm*—Greenblum & Bernstein, P.L.C.

(57) ABSTRACT

Slimming device capable of effectively activating an uncoupling protein to provide a good slimming action. The slimming device physically stimulates an uncoupling protein that is responsible for thermogenesis to activate the uncoupling protein, thereby generating heat. An uncoupling protein can be effectively activated by the physical stimulation.

36 Claims, 5 Drawing Sheets

SLIMMING DEVICE

FIELD OF THE INVENTION

This invention relates to a slimming device capable of providing a slimming action by a physical stimulation applied to the body.

BACKGROUND OF THE INVENTION

Many slimming devices have been available to afford the body a physical stimulation such as an ultrasonic, a low frequency, a high frequency, a pressure, a roller vibration, and a thermal stimulation. However, these slimming devices are not based on an adequate mechanism for providing a slimming action, and merely allow physical exercises for increasing the level of metabolism, or tentative translocation of a superflux of adipose to another part. Consequently, most of these slimming devices provide a slight increase in metabolic level, and it is unknown if these devices effectively provide a slimming action.

The primary purpose in obtaining a slimming action is to lower a superflux of adipose stored in the body, or to optimize the level of the adipose. In view of attaining the purpose, a superflux of adipose from an adipocyte is firstly allowed to dissolve in blood (referred to as lipolysis), and then the lipid components produced by lipolysis are required to be combusted in a muscle tissue. In order to effectively combust the lipid components, it is necessary to increase in metabolic level or enhance the individual daily basal metabolic level by means of much physical exercises or elongated duration of time of physical exercises. That indicates that a slimming action is provided by continuous efforts to rise consumption energy relative to ingestion energy.

Most of the slimming agents that have been recently prevalent contain an ingredient for enabling induction of lipolysis via a direct secretion of noradrenaline. However, the induction of lipolysis is not sufficient to obtain a slimming action unless the lipid components produced by lipolysis are successfully combusted. Since the basal metabolic level reaches the peak at an age of front of the twenties and thereafter decreases, the adipose in the body is liable to accumulate due to the poor ability to combust the produced components with increasing age, thus making it difficult to obtain an effective slimming action.

On the other hand, advance of development in the field of treatment for obesity and the discovery of uncoupling proteins (uncoupling protein family) that are responsible for thermogenesis have led to elucidation on the mechanisms of obesity from the viewpoint of energy consumption, and it has been recently revealed that the level of metabolism depends on activity of the uncoupling protein family, which exists in a brown adipocyte, a white adipocyte, a skeletal muscle, and the like. As acknowledged from the fact that therapeutic agents for treating obesity have been developed to activate an uncoupling protein, what is necessary to obtain a slimming action is to determine how to activate an uncoupling protein in order to combust effectively the lipid components produced by lipolysis.

SUMMARY OF THE INVENTION

The present invention has been developed in view of the foregoing background, and is directed to provide a slimming device capable of successfully activating an uncoupling protein so as to obtain an effective slimming action.

In one aspect, the present invention relates to a slimming device which comprises means for physical stimulation wherein the means for physical stimulation comprises physically stimulating an uncoupling protein that is responsible for thermogenesis to activate the same, thereby generating and/or dissipating the heat.

The means for physical stimulation is herein referred to as at least one of a thermal stimulator, an electrical stimulator, and a mechanical stimulator applied to a part to be stimulated, and specifically include an ultrasonic, a high frequency, a middle frequency, a low frequency, a vibration, a heating, a cooling, an electric, a pressure, a massage, a kneading, a clapping, and the like.

The means for physical stimulation may comprise stimulating an uncoupling protein in at least one of a brown adipocyte, a white adipocyte, and a skeletal muscle. Brown adipocyte refers to a constituent cell in a thermogenesis tissue, brown adipose tissue, which is acknowledged to cause obesity when the function of the tissue lowers, and is located at the interscapular region, the axilla, the nape of the neck, the surrounding artery, the surrounding kidney, and the like. White adipocyte refers to a constituent cell in white adipose tissue that constructs a majority of body adipose and determines a physical feature by forming a thick fat build-up at any part of the body. Skeletal muscle is a general word showing a muscle for moving skeletons of the body, and is located systemically such as at arms, legs, and bulges.

In an embodiment, the present invention encompasses the slimming device which comprises means for physical stimulation, wherein the means for physical stimulation comprises stimulating exclusively an uncoupling protein in a brown adipocyte particularly located at the interscapular region, the axilla, or the nape of the neck, and the slimming device which comprises means for physical stimulation, wherein the means for physical stimulation comprises stimulating exclusively an uncoupling protein in a white adipocyte or a skeletal muscle located at a part to be slimmed.

Alternatively, the invention relates to the slimming device which comprises means for physical stimulation, wherein the means for physical stimulation comprises stimulating an uncoupling protein in a brown adipocyte located at the interscapular region, the axilla, or the nape of the neck, as well as stimulating an uncoupling protein in a white adipocyte or a skeletal muscle located at a part to be slimmed. The slimming device includes an embodiment wherein a part to be slimmed and a brown adipocyte are simultaneously stimulated, and an embodiment wherein a part to be slimmed is firstly stimulated, and subsequently a brown adipocyte is stimulated within a defined period of time after the first stimulation, or vice versa.

In a preferred embodiment, the invention relates to the slimming device wherein the means for physical stimulation also comprises stimulating physically a sympathetic nerve to secrete a catecholamine at a part to be slimmed. More preferably, the invention relates to the slimming device that comprises, as the means for physical stimulation, an ultrasonic stimulation in which the ultrasonic stimulation not only secretes a catecholamine from the terminus of a sympathetic nerve and the adrenal medulla to induce lipolysis of a white adipose, but also activates an uncoupling protein in a white adipose or a skeletal muscle to decay locally the free fatty acids released by lipolysis with energy dissipation in the form of heat.

In a further aspect, the present invention relates to a method for slimming down or reducing weight, which comprises physically stimulating an uncoupling protein that is responsible for thermogenesis to activate the same, thereby generating and/or dissipating the heat. This embodiment includes the embodiments as mentioned above with respect to the slimming device of the present invention.

In a still further aspect, the present invention relates to a slimming device which comprises means for physical stimulation, wherein the means for physical stimulation comprises an ultrasonic stimulation in which the ultrasonic stimulation activates a sympathetic nerve to secrete a catecholamine, thereby inducing lipolysis of a white adipose, as well as a method therefor.

The invention also relates to a slimming device comprising a physical stimulation arrangement, the physical stimulation arrangement being structured to physically stimulate an uncoupling protein that is responsible for thermogenesis to activate the uncoupling protein, thereby generating heat.

The physical stimulation arrangement can comprise at least one of a thermal stimulator, an electrical stimulator, and a mechanical stimulator capable of being applied to a part to be stimulated.

The physical stimulation arrangement can be structured to stimulate an uncoupling protein in at least one of a brown adipocyte, a white adipocyte, and a skeletal muscle.

The physical stimulation arrangement can be structured to exclusively stimulate an uncoupling protein in a brown adipocyte located at the interscapular region, the axilla, or the nape of the neck.

The physical stimulation arrangement can be structured to exclusively stimulate an uncoupling protein in a white adipocyte or a skeletal muscle located at a part to be slimmed.

The physical stimulation arrangement can be structured to stimulate an uncoupling protein in a brown adipocyte located at the interscapular region, the axilla, or the nape of the neck, as well as an uncoupling protein in a white adipocyte or a skeletal muscle located at a part to be slimmed.

The physical stimulation arrangement can be structured to simultaneously stimulate an uncoupling protein in a brown adipocyte and an uncoupling protein at a part to be slimmed.

The physical stimulation arrangement can be structured to firstly stimulate an uncoupling protein at a part to be slimmed, and to subsequently stimulate an uncoupling protein in a brown adipocyte within a defined period of time after the first stimulation, or vice versa.

The physical stimulation arrangement can be structured to stimulate a sympathetic nerve to secrete a catecholamine at a part to be slimmed.

The physical stimulation arrangement can comprise ultrasonic stimulation, in which the ultrasonic stimulation not only secretes a catecholamine from the terminus of a sympathetic nerve and the adrenal medulla to induce lipolysis of a white adipose, but also activates an uncoupling protein in a white adipose or a skeletal muscle to decay locally free fatty acids released by lipolysis with energy dissipation in a form of heat.

BRIEF DESCRIPTION OF THE DRAWINGS

In FIGS. 5, 6 and 7, * means 95% confidence limits, and ** means 99% confidence limits.

FIG. 6 is a graph showing a relationship between a physical stimulation by ultrasonic irradiation and a weight of adipose.

FIG. 7 is a graph showing a relationship between a physical stimulation by ultrasonic irradiation and an amount of free fatty acids.

DETAILED DESCRIPTION OF THE PREFERRED EMBODIMENTS

Figure 1:
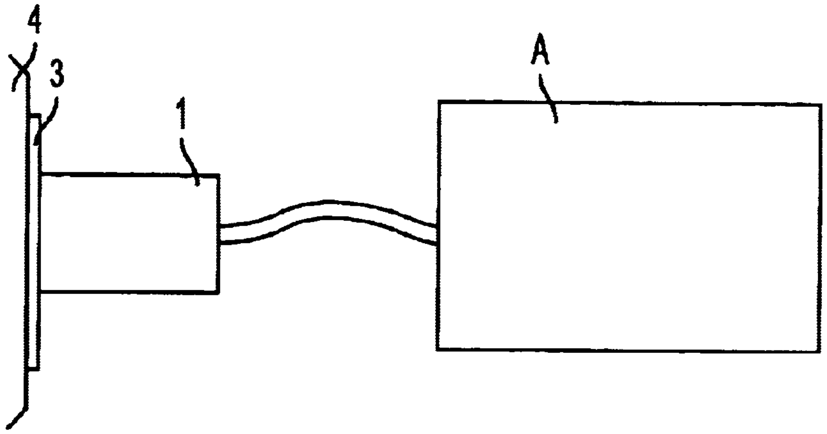
FIG. 1 depicts one embodiment for conducting the present invention. A represents a slimming device. Symbols 1, 3, and 4 represent an ultrasonicirradiator, a medium for ultra irradiation, and the body, respectively.

In order to accomplish a purpose of slimming, it is necessary as discussed above to induce lipolysis of a superflux of adipose from the body firstly, although the subsequent combustion of the lipid components produced by lipolysis is also necessary.

Lipolysis can be induced by secretion of a catecholamine, which is a general name of three substances, dopamine, noradrenaline, and adrenaline. A means for physical stimulation comprising physically stimulating a sympathetic nerve at a part to be slimmed enables secretion of a catecholamine from the terminus of a sympathetic nerve and the adrenal medulla, and also enables acceleration of the secretion. In addition to such indirect secretion of a catecholamine via the physical stimulation of a sympathetic nerve, a direct secretion of a catecholamine or an acceleration of the secretion may be accomplished by internal or external administration of a chemical stimulant such as caffeine and nicotine.

In this connection, it has been found that an ultrasonic successfully stimulates a sympathetic nerve to secrete a catecholamine, thereby inducing lipolysis. The embodiment may constitute the invention. This is demonstrated in Example 2 hereinafter. In order to induce lipolysis, (1) other physical stimulation such as a massage, and a heating may be combined with an ultrasonic stimulation, (2) two or more ultrasonic probes may be used alternately, (3) two or more ultrasonic probes may be slid on the skins, providing a massage stimulation as well as the ultrasonic stimulation, or (4) an ultrasonic stimulation may be effected at intervals to avoid any tolerance of the body to the ultrasonic radiation, thus increasing in the release of free fatty acids. Once lipolysis occurs, it is possible to use physical exercises, or a continuous ultrasonic stimulation in order to combust the produced lipid components for obtaining a slimming action.

In accordance with the present invention, the combustion of the lipid components produced by lipolysis can be attained by using a means for a physical stimulation to stimulate physically the body and activate an uncoupling protein (UCP) that is responsible for thermogenesis, thereby generating and/or dissipating the heat. UCP1, UCP2, and UCP3 have been known as an uncoupling protein, and studies on these uncoupling proteins have revealed that they exist in a brown adipocyte located at the interscapular region, the axilla, the nape of the neck, and the like tissue; a white adipocyte so-called adipose; and a skeletal muscle; or the like. Accordingly, in an embodiment of the present invention, the uncoupling protein may be physically stimulated by a physical stimulation of at least one of a brown adipocyte located at the interscapular region, the axilla, or the nape of the neck; or a white adipocyte or a skeletal muscle which are located at a part to be slimmed. The stimulation activates the uncoupling protein to generate and/or dissipate the heat, thereby obtaining a slimming action.

The physical stimulation to be applied to the body in order not only to activate the uncoupling protein but also to secrete a catecholamine includes thermal stimulation, electrical stimulation, and mechanical stimulation, and specifically includes an ultrasonic, a high frequency, a middle frequency, a low frequency, a vibration, a heating, a cooling, an electric, a pressure, a massage, a kneading, and a clapping, and the like. The slimming device of the present invention comprises means for at least one physical stimulation selected from a group consisting of these stimulations, which means is to be applied to the body.

In the case that a ultrasonic irradiation is selected among the means for physical stimulation as mentioned above, a sympathetic nerve can be stimulated to secrete a catecholamine from the terminus of a sympathetic nerve and the adrenal medulla, which catecholamine can induce lipolysis of an adipose from a white adipocyte, and besides an uncoupling protein in a white adipocyte and a skeletal muscle to be irradiated can be activated to decay the free fatty acids released by lipolysis at the irradiated part with energy dissipation in the form of heat. Accordingly, this embodiment makes it possible to securely reduce an adipose leading to an effective slimming action.

The slimming device of the present invention can be used to obtain a partial slimming action at the stimulated part by stimulating exclusively a part of the body to be slimmed to activate exclusively an uncoupling protein in a white adipocyte and a skeletal muscle at the part, thereby generating and dissipating the heat.

Further, the slimming device of the present invention can be also used to obtain a general slimming action. This is accomplished by stimulating exclusively a brown adipocyte located at the interscapular region, the axilla, or the nape of the neck to activate an uncoupling protein in the brown adipocyte. This physical stimulation of the brown adipocyte enables activation of uncoupling proteins that are spread over the systemic body, and generation and/or dissipation of the heat, thereby providing the general slimming action.

The slimming device may comprise both means for physical stimulation which comprises exclusively stimulating an uncoupling protein at a part to be slimmed, and means for physical stimulation which comprises stimulating exclusively an uncoupling protein at a brown adipocyte located at the interscapular region, the axilla, or the nape of the neck.

In case of the slimming device comprising the two means for physical stimulation as described above, both means for physical stimulation can be set up to effect the stimulations at the same time. Each means for a physical stimulation may be the same kind of stimulation or different from each other.

Alternatively, in case of the slimming device comprising the two means for a physical stimulation as described above, it is also possible that an uncoupling protein at a part to be slimmed is exclusively stimulated firstly, and subsequently an uncoupling protein at a brown adipocyte is exclusively stimulated within a defined period of time after the first stimulation, or vice versa. The defined period of time is a period of time for completing an activation of an uncoupling protein at a part to be slimmed, and preferably about 30 minutes or less.

In this case, each means for physical stimulation may be the same kind of stimulation or different each other.

As described above, the present invention simultaneously provides a general slimming action, and a partial slimming action at a part to be slimmed, by stimulating exclusively an uncoupling protein at a brown adipocyte, and stimulating exclusively an uncoupling protein at a part to be slimmed.

Particular embodiments for conducting the present invention are described below.

1) Slimming device A is constructed, which is equipped as a means for a physical stimulation with ultrasonic irradiator 1 that irradiates an ultrasonic in a condition of 1–3 MHz, 1 $W/cm^2$. As shown in FIG. 1, ultrasonic irradiator 1 is positioned on the surface of the part to be slimmed of body 4, and the ultrasonic is irradiated. It is preferable to apply ultrasonic medium 3 such as a gel externally to the part to be irradiated. The gel is the same as a gel used in a usual ultrasonic diagnosis, and is exemplified by a hydrophilic gel wherein water is retained in a carboxymethylcellulose. Ultrasonic irradiated from ultrasonic irradiator 1 reaches an adipose and a muscle through ultrasonic medium 3, and stimulates and activates uncoupling proteins in the adipose and the muscle, thereby obtaining a slimming action at the irradiated part.

Figure 2:
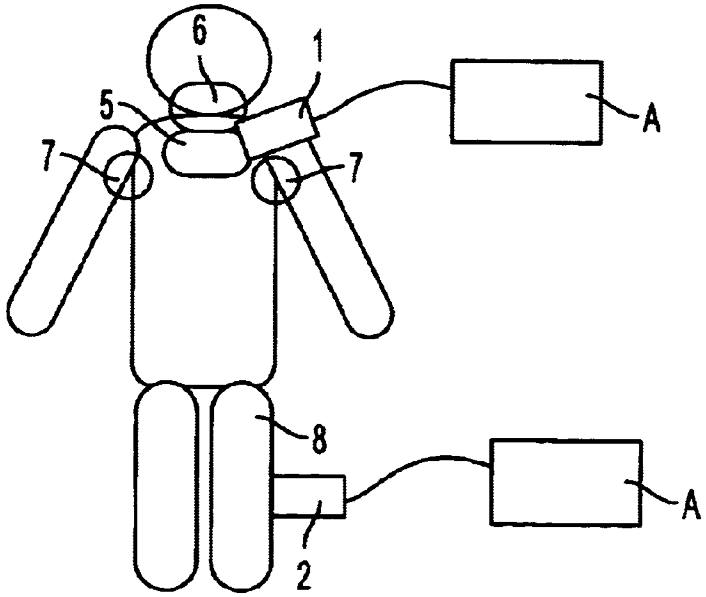
FIG. 2 depicts a further embodiment for conducting the present invention. A represents a slimming device. Symbols 1, 2, 5, 6, 7, and 8 represent ultrasonic irradiator, low frequency oscillator, scapula underpart, cervical rear, axilla, and leg, respectively.

2) Slimming device A is constructed, which is equipped as a means for a physical stimulation with ultrasonic irradiator 1 that irradiates an ultrasonic in a condition of 1–3 MHz, 1 $W/cm^2$, and with low frequency oscillator 2 evolving a low frequency in a condition of 1–1000 Hz, 5 mA. As shown in FIG. 2, ultrasonic irradiator 1 is used to stimulate at least one of scapula underpart 5, axilla 7, and cervical rear 6 of the body, thereby activating an uncoupling protein in a brown adipocyte located at the parts. Additionally, simultaneously with the stimulation, or within 30 minutes after the stimulation, low frequency oscillator 2 is used to stimulate a part to be slimmed, leg 8, thereby activating an uncoupling protein in a white adipocyte and a skeletal muscle located at the part. This provides the partial and the general slimming actions.

Several ultrasonic irradiators, and several low frequency oscillators can be used to stimulate many parts of the body. Further, it is possible that merely one apparatus of either ultrasonic irradiator or low frequency oscillator may be used to stimulate at least one of scapula underpart 5, axilla 7, and cervical rear 6 of the body, thus activating an uncoupling protein in a brown adipocyte located at the parts, followed by one or more parts to be slimmed, thus activating an uncoupling protein in a white adipocyte and a skeletal muscle located at the parts.

Figure 3:
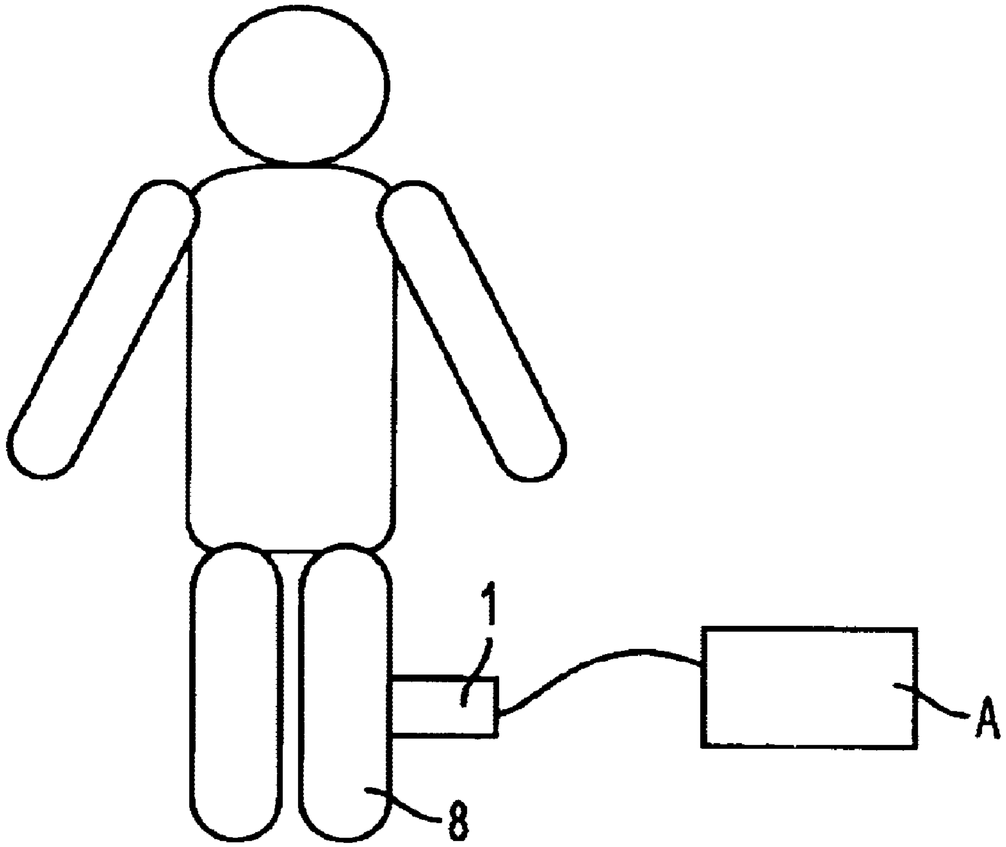
FIG. 3 depicts a still further embodiment for conducting the present invention.

3) Slimming device A is constructed, which is equipped as a means for a physical stimulation with ultrasonic irradiator 1 that irradiates an ultrasonic in a condition of 1–3 MHz, 1 $W/cm^2$. As shown in FIG. 3, ultrasonic irradiator 1 is used to stimulate a part to be slimmed, leg 8. This stimulation constitutes a stimulation of a white adipocyte and a skeletal muscle located at the part, and simultaneously, an acceleration of lipolysis and an activation of an uncoupling protein, thereby obtaining the partial slimming action at the part to be slimmed.

Several ultrasonic irradiators can be used to stimulate many parts to be slimmed at the same time.

More particular embodiments for conducting the present invention are described below.

Figure 4:
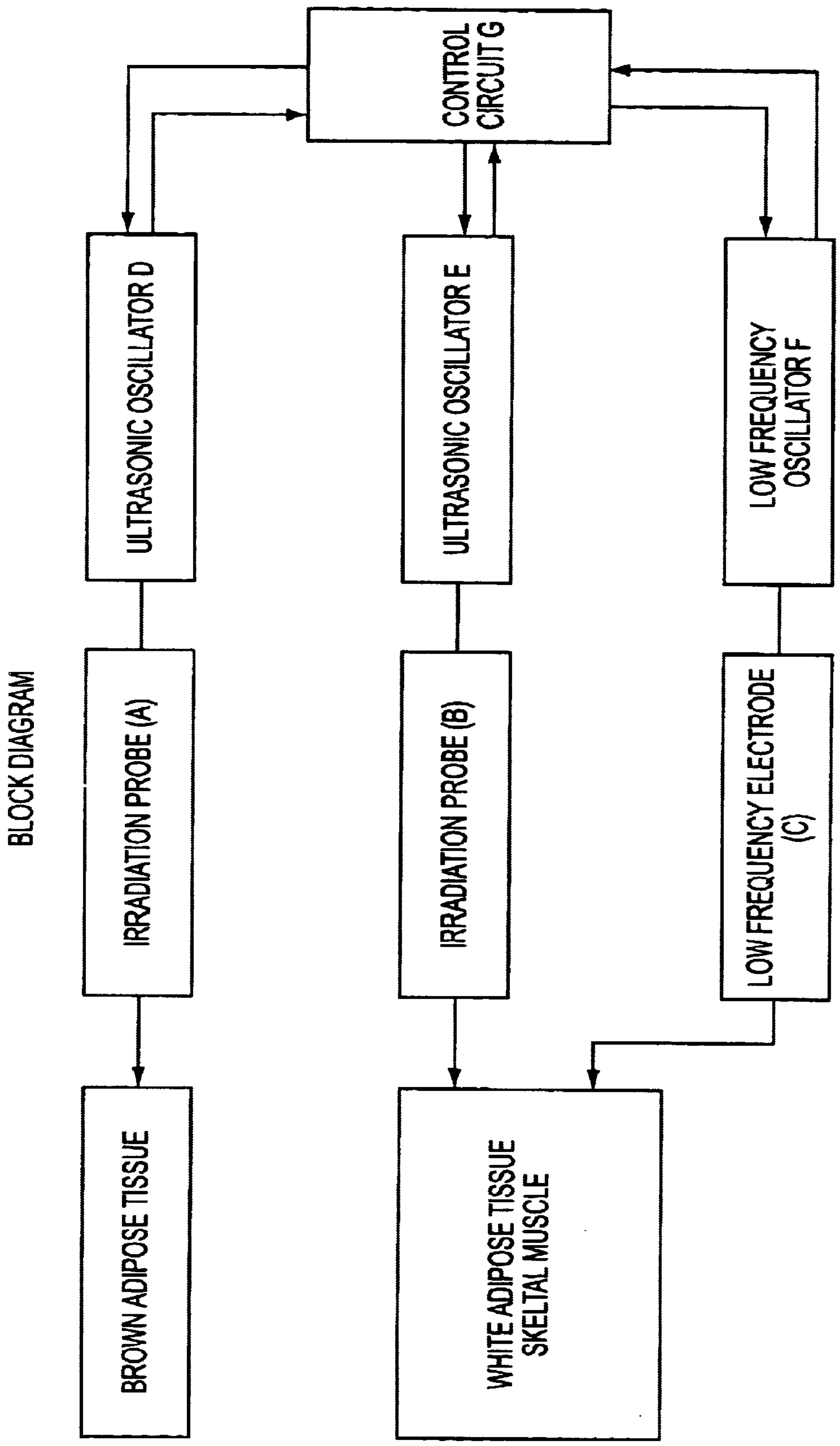
FIG. 4 is a block diagram showing an embodiment for a slimming device of the present invention.

1) As shown in FIG. 4, a brown adipose tissue is stimulated with irradiation probe A to obtain a general slimming action. Ten minutes after the irradiation, during which UPC is expected to be sufficiently activated, ultrasonic oscillator D is controlled with control circuit G to quench or to down-regulate the ultrasonic.

Then, a part to be slimmed is irradiated with an ultrasonic from ultrasonic probe B, while controlling the ultrasonic with ultrasonic oscillator E via control circuit G in respect to a frequency, an output power, and a period of irradiation time so that they are suitable for the part to be slimmed. At this time, a low frequency stimulation can be applied to the part to be slimmed in stead of the ultrasonic irradiation. Similarly to the ultrasonic irradiation, the low frequency is controlled with low frequency oscillator F via control circuit G in respect to a frequency, a current value, and a period of stimulation time so that they are suitable for the part to be slimmed, and the stimulation is outputted from low frequency electrode C.

2) Alternatively, in order to obtain a general slimming action, a brown adipose tissue is stimulated with irradiation probe A, and ten minutes after the irradiation, during which UPC is expected to be sufficiently activated, any aerobic exercise can be carried out to combust the lipid components produced by lipolysis.

3) In order to obtain a partial slimming action, either ultrasonic irradiation probe B or low frequency electrode C can be solely applied to a part to be slimmed.

EXAMPLES

For further descriptions of the present invention, the following examples are presented, but these examples should not be construed to limit the scope of the invention.

Example 1

A slimming action obtained by an irradiation of ultrasonic was demonstrated by the following experiments.

Figure 5:
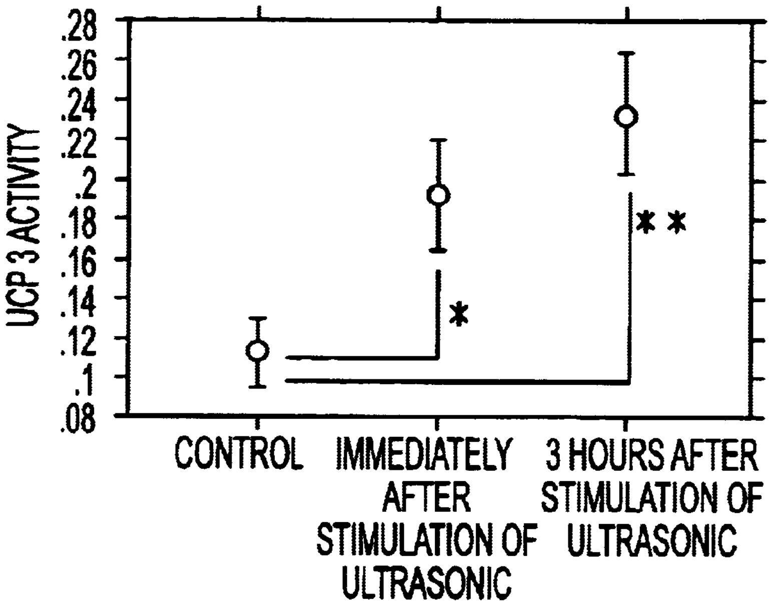
FIG. 5 is a graph showing a relationship between a physical stimulation by ultrasonic irradiation and an activity of UPC3.

Six rats were irradiated at their legs with an ultrasonic of 1 MHz, 1 W/cm$^2$ for 20 minutes, and activity of UCP3 in the skeletal muscle of the irradiated legs was determined by Northern blotting immediately and three hours after completion of the irradiation. The results are shown in FIG. 5, which shows each UCP3 activity in the irradiated parts at the two time points, and also UCP3 activity of unirradiated six rats as a control. This demonstrates that the physical stimulation by the ultrasonic significantly activated the UCP3.

Figure 6:
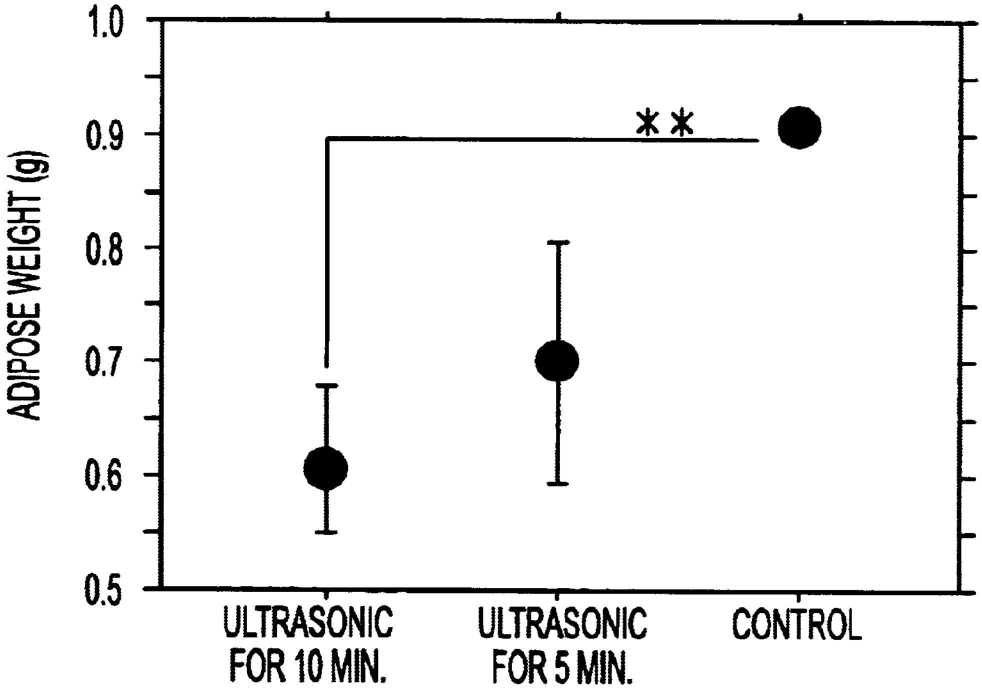

Then, four rats were irradiated at their legs with an ultrasonic of 1 MHz, 1 W/cm$^2$ for five minutes, or for ten minutes per day over four weeks, and then, the weight of the excised subcutaneous adipose at the irradiated parts was determined. The results are shown in FIG. 6, which shows each adipose weight of the rats irradiated for five minutes per day, and the rats irradiated for ten minutes per day, and also adipose weight of unirradiated four rats as a control. This demonstrates that the physical stimulation by the ultrasonic significantly lowered the adipose weight, and provided the slimming action.

Example 2

Ultrasonic irradiator having an ultrasonic oscillator was used as a means for a physical stimulation to stimulate a sympathetic nerve, thereby secreting a catecholamine leading to induction of lipolysis.

Figure 7:
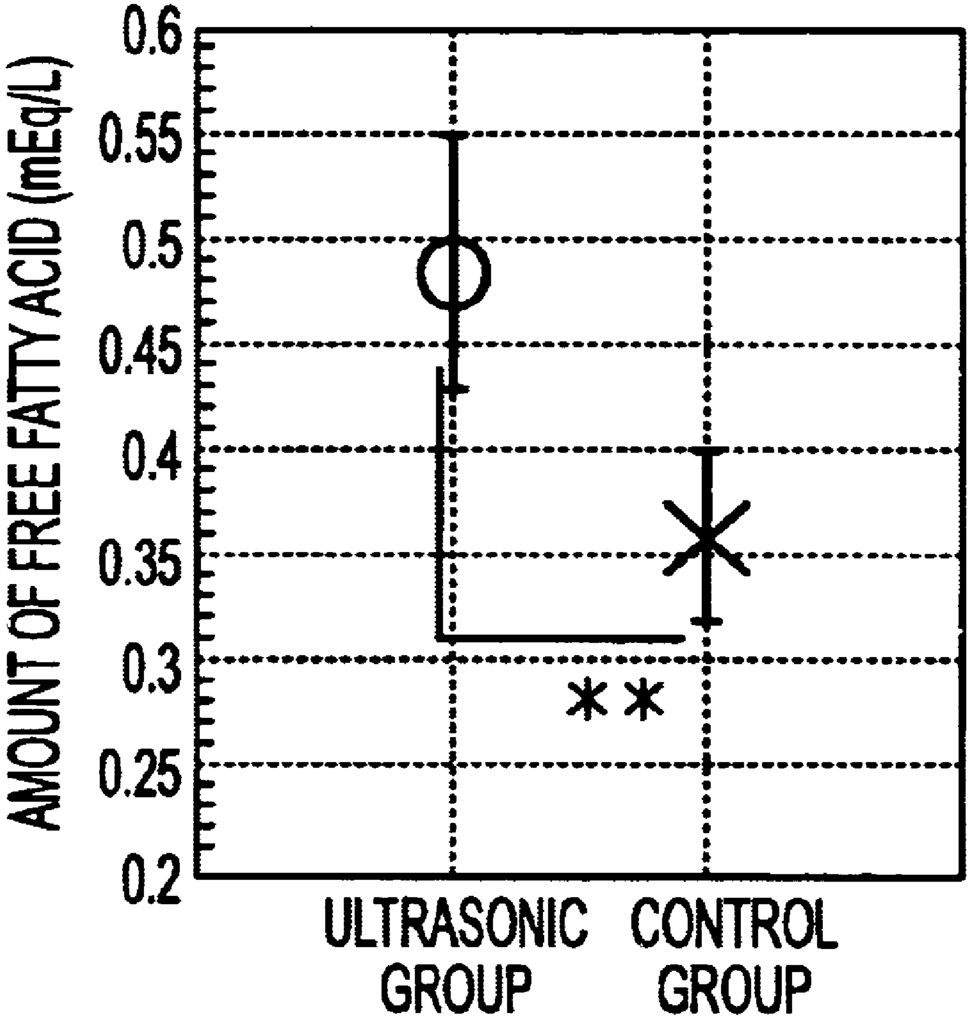

Six rats were irradiated with an ultrasonic in a condition of 1 MHz, 1 W/cm$^2$ for 10 minutes (ultrasonic group), and other six rats not receiving ultrasonic served as controls (control group). Then, amount of free fatty acids in blood was determined in each of the ultrasonic group and the control group. The results are shown in FIG. 7, which shows that the amount of free fatty acids in the ultrasonic group significantly increased relative to the control group, demonstrating that the physical stimulation by the ultrasonic accelerates lipolysis.

The present disclosure relates to subject matter contained in priority Japanese Patent Application No. 364324/1999, filed on Dec. 22, 1999, the contents of which is herein expressly incorporated by reference in its entirety.

What is claimed is:

1. A slimming device comprising means for physical stimulation wherein the means physically stimulate an uncoupling protein that is responsible for thermogenesis to activate the uncoupling protein, thereby generating heat.

2. The slimming device of claim 1, wherein the means for physical stimulation comprises at least one of a thermal stimulator, an electrical stimulator, and a mechanical stimulator capable of being applied to a part to be stimulated.

3. The slimming device of claim 1, wherein the means for physical stimulation comprises stimulating an uncoupling protein in at least one of a brown adipocyte, a white adipocyte, and a skeletal muscle.

4. The slimming device of claim 3, wherein the means for physical stimulation comprises exclusively stimulating an uncoupling protein in a brown adipocyte located at the interscapular region, the axilla, or the nape of the neck.

5. The slimming device of claim 3, wherein the means for physical stimulation comprises exclusively stimulating an uncoupling protein in a white adipocyte or a skeletal muscle located at a part to be slimmed.

6. The slimming device of claim 3, wherein the means for physical stimulation comprises stimulating an uncoupling protein in a brown adipocyte located at the interscapular region, the axilla, or the nape of the neck, as well as an uncoupling protein in a white adipocyte or a skeletal muscle located at a part to be slimmed.

7. The slimming device of claim 6, wherein the means for physical stimulation comprises simultaneously stimulating an uncoupling protein in a brown adipocyte and an uncoupling protein at a part to be slimmed.

8. The slimming device of claim 6, wherein the means for physical stimulation comprises stimulating firstly an uncoupling protein at a part to be slimmed, and subsequently stimulating an uncoupling protein in a brown adipocyte within a defined period of time after the first stimulation, or vice versa.

9. The slimming device of claim 1, wherein the means for physical stimulation comprises stimulating a sympathetic nerve to secrete a catecholamine at a part to be slimmed.

10. The slimming device of claim 9, wherein the means for physical stimulation comprises ultrasonic stimulation, in which the ultrasonic stimulation not only secretes a catecholamine from the terminus of a sympathetic nerve and the adrenal medulla to induce lipolysis of a white adipose, but also activates an uncoupling protein in a white adipose or a skeletal muscle to locally decay free fatty acids released by lipolysis with energy dissipation in a form of heat.

11. A slimming device comprising a physical stimulation arrangement, said physical stimulation arrangement being structured to physically stimulate an uncoupling protein that is responsible for thermogenesis to activate the uncoupling protein, thereby generating heat.

12. The slimming device of claim 11 .wherein the physical stimulation arrangement comprises at least one of a thermal stimulator, an electrical stimulator, and a mechanical stimulator capable of being applied to apart to be stimulated.

13. The slimming device of claim 12, wherein the physical stimulation arrangement is structured to stimulate a sympathetic nerve to secrete a catecholamine at a part to be slimmed.

14. The slimming device of claim 11, wherein the physical stimulation arrangement is structured to stimulate an uncoupling protein in at least one of a brown adipocyte, a white adipocyte, and a skeletal muscle.

15. The slimming device of claim 14, wherein the physical stimulation arrangement is structured to exclusively stimulate an uncoupling protein in a brown adipocyte located at the interscapular region, the axilla, or the nape of the neck.

16. The slimming device of claim 14, wherein the physical stimulation arrangement is structured to exclusively stimulate an uncoupling protein in a white adipocyte or a skeletal muscle located at a part to be slimmed.

17. The slimming device of claim 16, wherein the physical stimulation arrangement is structured to stimulate a sympathetic nerve to secrete a catecholamine at a part to be slimmed.

18. The slimming device of claim 14, wherein the physical stimulation arrangement is structured to stimulate an uncoupling protein in a brown adipocyte located at the interscapular region, the axilla, or the nape of the neck, as well as an uncoupling protein in a white adipocyte or a skeletal muscle located at a part to be slimmed.

19. The slimming device of claim 18, wherein the physical stimulation arrangement is structured to simultaneously stimulate an uncoupling protein in a brown adipocyte and an uncoupling protein at a part to be slimmed.

20. The slimming device of claim 19, wherein the physical stimulation arrangement is structured to stimulate a sympathetic nerve to secrete a catecholamine at a part to be slimmed.

21. The slimming device of claim 18, wherein the physical stimulation arrangement is structured to firstly stimulate an uncoupling protein at a part to be slimmed, and to subsequently stimulate an uncoupling protein in a brown adipocyte within a defined period of time after the first stimulation, or vice versa.

22. The slimming device of claim 21, wherein the physical stimulation arrangement is structured to stimulate a sympathetic nerve to secrete a catecholamine at a part to be slimmed.

23. The slimming device of claim 18, wherein the physical stimulation arrangement is structured to stimulate a sympathetic nerve to secrete a catecholamine at a part to be slimmed.

24. The slimming device of claim 14, wherein the physical stimulation arrangement is structured to stimulate a sympathetic nerve to secrete a catecholamine at a part to be slimmed.

25. The slimming device of claim 11, wherein the physical stimulation arrangement is structured to stimulate a sympathetic nerve to secret a catecholamine at a part to be slimmed.

26. The method of claim 25, wherein the physical stimulation arrangement comprises ultrasonic stimulation, in which the ultrasonic stimulation not only secretes a catecholamine from the terminus of a sympathetic nerve and the adrenal medulla to induce lipolysis of a white adipose, but also activates an uncoupling protein in a white adipose or a skeletal muscle to decay locally free fatty acids released by lipolysis with energy dissipation in a form of heat.

27. A method for slimming down or reducing weight, comprising physically stimulating an uncoupling protein that is responsible for thermogenesis to activate the uncoupling protein, thereby generating heat.

28. The method of claim 27, wherein the physical stimulation of the uncoupling protein comprises at least one of thermal stimulation, electrical stimulation, and mechanical stimulation.

29. The method of claim 27, wherein the physical stimulation of the uncoupling protein comprises stimulating at least one of a brown adipocyte, a white adipocyte, and a skeletal muscle.

30. The method of claim 29, wherein the physical stimulation of the uncoupling protein comprises exclusively stimulating a brown adipocyte located at the interscapular region, the axilla, or the nape of the neck.

31. The method of claim 29, wherein the physical stimulation of the uncoupling protein comprises exclusively stimulating a white adipocyte or a skeletal muscle located at a part to be slimmed.

32. The method of claim 29, wherein the physical stimulation of the uncoupling protein comprises stimulating a brown adipocyte located at the interscapular region, the axilla, or the nape of the neck, as well as a white adipocyte or a skeletal muscle located at a part to be slimmed.

33. The method of claim 32, wherein the physical stimulation of the uncoupling protein comprises simultaneously stimulating a brown adipocyte and a part to be slimmed.

34. The method of claim 32, wherein the physical stimulation of the uncoupling protein comprises stimulating firstly a part to be slimmed, and subsequently stimulating a brown adipocyte within a defined period of time after the first stimulation, or vice versa.

35. The method of claims 27 wherein the physical stimulation of the uncoupling protein comprises stimulating a sympathetic nerve to secrete a catecholamine at a part to be slimmed.

36. The method of claim 35, wherein the physical stimulation of the uncoupling protein comprises an ultrasonic stimulation, in which the ultrasonic stimulation not only secretes a catecholamine from the terminus of a sympathetic nerve and the adrenal medulla to induce lipolysis of a white adipose, but also activates an uncoupling protein in a white adipose or a skeletal muscle to locally decay free fatty acids released by lipolysis with energy dissipation in the form of heat.

* * * * *

UNITED STATES PATENT AND TRADEMARK OFFICE

CERTIFICATE OF CORRECTION

PATENT NO. : 6,645,229 B2
DATED : November 11, 2003
INVENTOR(S) : Y. Matsumura et al.

It is certified that error appears in the above-identified patent and that said Letters Patent is hereby corrected as shown below:

Column 8,
Line 63, "apart" should be -- a part --.

Column 9,
Line 52, "secret" should be -- secrete --.

Signed and Sealed this

Twentieth Day of April, 2004

JON W. DUDAS
*Acting Director of the United States Patent and Trademark Office*